United States Patent [19]

Charbardes et al.

[11] Patent Number: 5,266,708

[45] Date of Patent: Nov. 30, 1993

[54] NEW INTERMEDIATES, PROCESS FOR THEIR PREPARATION, AND THEIR USE FOR THE SYNTHESIS OF VITAMINS A AND E

[75] Inventors: Pierre F. Charbardes, Sainte Foy Les Lyon; Lucette Duhamel; Pierre Duhamel, both of Mont Saint Aignan; Jerome Guillemont, Beuzeville; Jean-Marie Poirier, Saint Martin du Vivier, all of France

[73] Assignee: Rhone-Poulenc Nutrition Animale, Commentry, France

[21] Appl. No.: 858,621

[22] Filed: Mar. 27, 1992

Related U.S. Application Data

[62] Division of Ser. No. 620,854, Dec. 3, 1990, Pat. No. 5,120,864.

[30] Foreign Application Priority Data

Dec. 1, 1989 [FR] France ................................ 89 15870

[51] Int. Cl.$^5$ .................... C07D 319/06; C07D 317/18
[52] U.S. Cl. .................................... 549/369; 549/221; 549/357; 549/374; 549/378; 549/429; 549/430; 549/453; 549/455
[58] Field of Search ............... 549/369, 455, 357, 380, 549/430, 408

[56] References Cited

U.S. PATENT DOCUMENTS

| | | | |
|---|---|---|---|
| 2,816,117 | 12/1957 | Cawley | 549/374 |
| 4,268,444 | 5/1981 | Jaedicke | 549/374 |

FOREIGN PATENT DOCUMENTS

| | | | |
|---|---|---|---|
| 2842715 | 10/1980 | Fed. Rep. of Germany | 549/374 |
| 2917413 | 11/1980 | Fed. Rep. of Germany | 549/369 |
| 56-71085 | 6/1981 | Japan | 549/453 |
| 98203 | 6/1982 | Japan | 549/369 |
| 77837 | 5/1983 | Japan | 549/369 |

OTHER PUBLICATIONS

Kumadaki et al, Chem. Pharm. Bull. 1987, 515–520.

*Primary Examiner*—Glennon H. Hollrah
*Assistant Examiner*—Shailendra Kumar
*Attorney, Agent, or Firm*—Finnegan, Henderson, Farabow, Garrett & Dunner

[57] ABSTRACT

New intermediates and processes for the preparation of vitamins A and E, which are the acetals of 5,6-dihalo-3-methyl-3-hydroxyhexanal or of 6-halo-3-hydroxy-3-methyl-5-hexenal or 3-methyl-3-hydroxy-5-hexenal, as well as processes for making the intermediates. After dehydrohalogenation and dehydration these intermediates are condensed directly with $\beta$-ionone or with 2-methyl-2-heptene-6-one to synthesize vitamins A and E respectively.

1 Claim, No Drawings

NEW INTERMEDIATES, PROCESS FOR THEIR PREPARATION, AND THEIR USE FOR THE SYNTHESIS OF VITAMINS A AND E

This is a division of application Ser. No. 07/620,854, filed Dec. 3, 1990, now U.S. Pat. No. 5,120,864.

This application is related to French Patent Application No. 8915870, filed Dec. 1, 1989, the disclosure of which is entirely incorporated by reference herein.

The present invention relates to novel intermediates for the preparation of vitamins, to processes for preparing these intermediates and to the use of these intermediates for the synthesis of vitamins A and E. These novel intermediates contain 7 carbon atoms and can be condensed directly with β-ionone or with sulphones containing 13 carbon atoms to prepare vitamin A.

Several known processes for the preparation of vitamin A involve condensing directly a derivative containing 7 carbon atoms. One process is disclosed in European Patent 242,247, which involves the condensation of 6-bromo-3-methyl-1-trialkylsilyloxyhexatriene with β-ionone. Although adequate in the preparation of vitamin A, the prohibitive cost of the silylated raw material renders this process disadvantageous. This process uses raw materials such as bromomethyltriphenyl-phosphonium bromide. Further, the preparation of the silylated derivative from 5,5-dimethoxy-3-methyl-2-pentenal requires three stages, some of these stages being very long. This process also makes it possible to obtain only overall yields which do not exceed 30% of silylated derivative from a derivative containing 6 carbon atoms.

Another process for the preparation of vitamin A begins with the lithium derivative of the compound containing 7 carbon atoms, which consists of bringing the derivative into contact with β-ionone. The raw material containing 7 carbon atoms is 6-bromo-3-methyl-1,1-dimethoxy-3,5-hexadiene, being prepared from bromomethyltriphenylphosphonium, prepared according to the paper published in Tetrahedron Letters (Matsumoto, Kurode, 21:4021 (1980)) and from 1,1-dimethoxy-3-methyl-2-pentenal, which is itself prepared according to British Patent GB 1,591,968 from an alcohol orthoformate and from an enoxysilane containing an alkenyl chain containing 4 carbon atoms. Similarly, this process involving the preparation of these derivatives containing 7 carbon atoms appears particularly long and costly.

Although use of these known processes for the preparation of vitamins A and E has proven adequate, it has not been apparent that any of these processes or the materials used therein could overcome the problems inherent in these materials, particularly the expense of the raw materials. Industry has been searching for a long time for a relatively simpler process for the preparation of at least vitamin A starting from inexpensive raw materials.

In accordance with the invention, novel materials and processes enable vitamin A or vitamin E to be synthesized from inexpensive and available raw material, such as from the dimethyl acetal of acetylacetaldehyde. One of the preferred classes of compounds according to the invention contains 7 carbon atoms and corresponds to the following general formula (I):

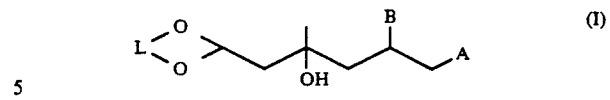

wherein L denotes an alkylene radical containing 2 to 3 carbon atoms, optionally substituted by one or more alkyl, alkylene or alkoxy groups containing 1 to 4 carbon atoms; A denotes a halogen chosen from chlorine, bromine and iodine and/or a covalent bond with B; and B denotes a halogen chosen from chlorine, bromine and iodine or a covalent bond with A.

Among these compounds containing 7 carbon atoms, compounds in which L denotes an alkylene group and the halogen is bromine are preferred. Further, compounds which are especially preferred are: 1,1-ethylenedioxy-3-hydroxy-3-methyl-5-hexene; 5,6-dibromo-1,1-ethylenedioxy-3-methyl-3-hexano and 6-bromo-1,1-ethylenedioxy-3-hydroxy-3-methyl-5-hexene.

According to an aspect of the invention, a process for the preparation of the compounds of formula (I) in which A is covalent bond with B consists in a first stage in bringing the dialkyl acetal of acetylacetaldehyde denoted by the formula (A):

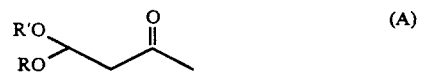

where each of R and R' denotes a linear or branched alkyl group containing 1 to 4 carbon atoms which is identical or different, into contact with a dialcohol in the presence of an acidic catalyst.

The dialcohol is preferably an aliphatic dialcohol containing 2 to 3 carbon atoms optionally substituted by a number of alkyl, alkylene or alkoxy groups containing 1 to 4 carbon atoms. Dialcohols which are preferred are ethylene glycol, propylene glycol, ethanediol derivatives of formula:

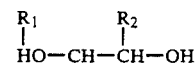

and propanediol derivatives of formula:

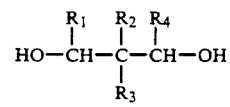

where $R_1$, $R_2$, $R_3$ and $R_4$ denote identical or different groups chosen from alkyl, alkylene and alkoxy radicals containing 1 to 4 carbon atoms. Further, two alkylene groups R may form an alicyclic ring. The use of ethylene glycol is very particularly preferred.

Also, preferred acidic catalyst is chosen especially from the Lewis acids (such as zinc or aluminum chloride, or boron trifluoride) and para-toluenesulphonic acid.

The second stage of the process of preparation comprises bringing the product obtained in the first stage, which is preferably 1,1-ethylenedioxy-3-butanone, into contact with an allylmagnesium halide, preferably chloride. This reaction is preferably carried out in a solvent which is inert under the reaction conditions at a temperature of between −20° C. and 0° C., such as ethers.

In accordance with another aspect of the invention, a process is provided for the preparation of the compounds of formula (I), wherein each of A and B is a halogen, consists in bringing the 1,1-alkylenedioxy-3-hydroxy-3-methyl-5-hexene into contact with molecular halogen. This reaction is preferably carried out in a solvent which is inert under the reaction conditions, at a temperature of between −20° C. and 10° C., in the presence of a weak base, such as alkali metal carbonates such as aliphatic or aromatic halogenated solvents (such as carbon tetrachloride or chlorobenzenes).

In accordance with another aspect of the invention, a process for the preparation of the compounds of formula (I) is provided in which A denotes a halogen and B denotes a covalent bond with A, consists in treating the above crude product with a strong base, such as potassium tert-butylate.

In accordance with other embodiments of the invention, the derivatives of formula (I) in which each of A and B denotes a halogen are employed for the preparation of retinal or of vitamin E by a process comprising in eliminating a halogen and the hydroxyl group by means of a base preferably chosen from tertiary amines, alcoholates and a halide, such as methanesulphonyl chloride or phosphorus oxychloride (POCl₃). The derivative obtained, the 6-halo-1,1-alkylene-dioxy-3-methyl-3,5-hexadiene, can be condensed after transmetalation by means of an alkyllithium with β-ionone which, after dehydroxylation and deprotection by means of a strong acid in an organic solvent, preferably acetone, gives retinal. The 6-halo-1,1-alkylenedioxy-3-methyl-3,5-hexadiene also gives dihydrofarnesal after condensation with 2-methyl-2-heptene-6-one and dehydration.

The compounds of formula (I) in which A denotes a halogen and B a covalent bond with A are, in their case, also employed for the synthesis of vitamin A or E by a process similar to that described above, which consists in performing a dehydration by means of a base chosen preferably from tertiary amines, alcoholates and a halide such as methanesulphonyl halide or phosphorus oxychloride. They produce the 6-halo-1,1-alkylenedioxy-3-methyl-3,5-hexadiene in the same way.

The derivative of formula (I) in the case of which A and B denote a halogen can be deprotected and dehydroxylated by employing a strong acid in an organic solvent, preferably acetone. This then yields 6-bromo-3-methyl-2,4-hexadienal which, after protection with an aliphatic dialcohol containing 2 to 3 carbon atoms or a mixed orthoformate obtained by condensing an orthoformate with a glycol, gives a new product which is the 6-halo-1,1-alkylenedioxy-3-methyl -2,4-hexadiene denoted by the general formula (II):

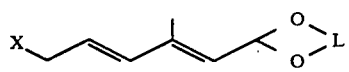  (II)

in which X and L have the same meaning as in the formula (I). This compound of formula (II) is condensed with a sulphone of formula (D):

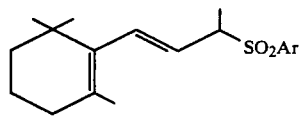  (D)

in which Ar denotes an aromatic radical, in the presence of a basic agent chosen from alkali metal hydroxides, alcoholates and hydrides or amides to give retinal after hydrolysis.

After condensation with an alkyl phosphite, the derivative of formula (II) gives a new intermediate of formula (III):

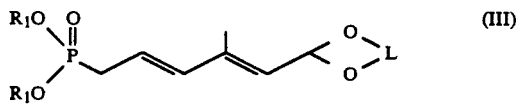  (III)

in which R₁ denotes a linear or branched alkyl group containing 1 to 6 carbon atoms, preferably an ethyl group.

This compound of formula (III) is condensed directly with β-ionone in the presence of a base in a solvent to produce retinal dioxolane; the latter is treated with a strong acid in a solvent to obtain retinal. By starting with 2-methyl-2-heptene-6-one, dihydrofarnesal can be produced which is an important intermediate in the synthesis of vitamin E.

To illustrate the nature of the invention, the following examples are given. It should be understood, however, that the invention is not to be limited to the specific conditions o details set forth in these examples.

EXAMPLE 1: Production of Hydroxyacetals Corresponding to Formula (I)

Formation of the basic "C7" skeleton: Freshly distilled ethylene glycol (31 g, 0.5 mol) and 1,1-dimethoxy-3-butanone (72.6 g, 0.55 mol) were heated to 65° C. in a 100-ml Claisen flask in the presence of a catalytic quantity of paratoluenesulphonic acid (100 mg). The methanol released during the transacetalization was collected. Once the theoretical volume (32 ml) was obtained, the ketoacetal was distilled under reduced pressure. The following was thus prepared in an 80% yield:

A. 1,1-Ethylenedioxy-3-butanone (A)

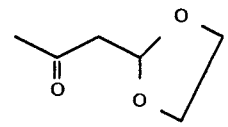

Magnesium turnings (14.6 g, 0.6 mol) and anhydrous ether (100 ml) were introduced into a dry one-litre reactor fitted with mechanical stirring, a thermometer, an Allihn condenser and a dropping funnel. The pure halide (3 g of allyl chloride) was added first of all. The formation of the magnesium derivative was characterized by the appearance of a cloudiness in the solution and of an increase in the temperature. The remainder of the halogenated derivative (29.1 g, i.e. 32.1 g) (0.42 mol) in all), diluted in anhydrous ether (200 ml) was added over 60 minutes at 0° C. To prevent the magnesium derivative from setting solid, ether (200 ml) was added (in 50-ml portions) during the addition of allyl chloride. After the addition, stirring was continued further for 30 minutes at room temperature. The concentration of the magnesium compound was then of the order of 0.84 mol/l

B. 1,1-Ethylenedioxy-3-hydroxy-3-methyl-5-hexene (B)

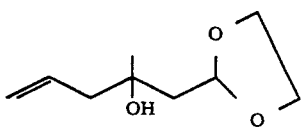

1,1-ethylenedioxy-3-butanone (51.6 g, 0.4 mol) diluted in ether (100 ml) was added slowly to the ether solution of the allylmagnesium derivative at the reflux temperature of ether. Stirring was carried out for 45 minutes.

The reaction mixture was cooled to 0° C. before being hydrolysed with the aid of a 10% strength aqueous solution (100 ml) of ammonium chloride. A precipitate was then seen to form, making it easier to withdraw the ether phase. The solid was taken up in water (half a litre) and was extracted with ether (3×200 ml). The ether phases were combined and concentrated. The residue was distilled. 1,1-ethylene-3-hydroxy-3-methyl-5-hexene was obtained.

Yld.: 80%. B.p.: 110° C./18 mm Hg.
IR: 3600-3200 ($\nu$ OH); 1640 ($\nu$ C=C).

C. 5,6-dibromo-1,1-ethylenedioxy-3-methyl-3-hexanol (C)

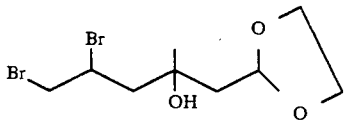

Hydroxyacetal (10 mmol) in carbon tetrachloride (40 ml) and sodium carbonate (1.06 g, 10 mmol) were introduced in succession into a 250-ml three-necked conical flask fitted with a septum, a thermometer and a dropping funnel. Bromine (1.06 g, 10 mmol) in solution in solvent (3 ml) was added over 5 min with stirring at a temperature of +3° C. An immediate bleaching of the bromine solution in contact with the reaction mixture was observed. After the introduction of bromine, stirring was performed for 20 min at this temperature.

After filtration to remove the insoluble products, the organic phase was washed with a saturated aqueous solution of sodium hydrogen carbonate (15 ml). An extraction with ether was carried out, and the extract was dried over magnesium sulphate and concentrated. The residue was purified by flash chromatography. 5,6-dibromo-1,1-ethylenedioxy-3-methyl-3-hexanol was obtained (25/100 ether/petroleum ether eluent) in an 80% yield.

D. 6-bromo-1,1-ethylenedioxy-3-hydroxy-3-methyl-5-hexene (D)

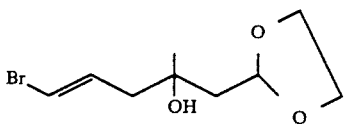

The crude product of the bromination of the hydroxydioxolane (C) was introduced, in a solution in anhydrous tetrahydrofuran (40 ml) into a conical flask under inert atmosphere. The temperature was lowered to −60° C, and tert-butanol (0.81 g, 11 mmol) in solution in THF (1 ml) was added. Potassium tert-butylate (1.23 g, 11 mmol) was added in small portions over 20 minutes. The mixture was left at this temperature for two hours; the solution, initially colourless, turned brown. Water (15 ml) was added quickly at this same temperature and the reaction mixture was stirred vigorously for 30 minutes. After taking up with ether (50 ml), the aqueous phase was extracted with ether (7×20 ml). The extract was dried over a magnesium sulphate and concentrated. The residue was then purified by flash chromatography. The hydroxydioxolane containing vinylic bromine (D) was isolated.

Eluent: 40/100 ether/petroleum other.
Yld: 56%. IR: 3600-3200 ($\nu$ OH); 1620 ($\nu$ C=C).

E. In-situ bromination and dehydrohalogenation without isolating (C)

Hydroxyacetal (B) (10 mmol) in carbon tetrachloride (40 ml) was introduced successively into a 250-ml three-necked conical flask fitted with a septum, a thermometer and a dropping funnel. Bromine (1.76 g, 11 mmol) in solution in solvent (3 ml) was added over 5 minutes with stirring at a temperature of +3° C. Stirring was carried out for 20 minutes at this temperature.

The reaction mixture was then diluted with anhydrous tetrahydrofuran (40 ml) and the temperature was lowered to −60° C. tert-butanol (0.81 g, 11 mmol) in solution in THF (1 ml) was added, followed by potassium tert-butylate (1.68 g, 15 mmol) still in small portions. A rise to −20° C. was allowed to take place slowly over one hour. The solution turned dark brown.

The hydrolysis using water (25 ml), at −20° C. was carried out. An extraction with ether was carried out (7×20 ml), and the extract was dried over magnesium sulphate and concentrated. The residue was purified by flash chromatography. 51% of acetal containing vinylic bromine (D) was isolated in this case.

EXAMPLE 2: Synthesis of Retinal

A. Dehydration of the hydroxyacetals (B) and (D)

Triethylamine (7 g, 69 mmol) was added to a 100-ml three-necked reactor fitted with a thermometer, a dropping funnel and a condenser, containing a solution of hydroxyacetal (20 mmol) in dichloromethane (50 ml), followed over 20 minutes by mesyl chloride (5.3 g, 46 mmol) diluted in dichloromethane (5 ml). The reaction was exothermic and a triethylamine hydrochloride precipitate appeared. The mixture was allowed to return to room temperature (1 hour) before being treated with distilled water (50 ml). It was extracted with dichloromethane (5×20 ml), and the solution was dried over magnesium sulphate and concentrated. The crude product was purified by flash chromatography. The following was obtained:

(1) From (B) 3-methyl-3,5-hexadienal dioxolane

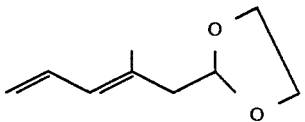

Eluent: 10/100 ether/petroleum ether.
Yld: 64%. IR: 1640 ($\nu$ C=C).

(2) From (D) 6-bromo-3-methyl-3,5-hexadienal dioxolane (E)

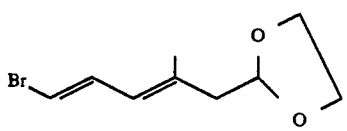

Eluent: 10/100 ether/petroleum ether.
Yld: 61%. IR: 1670-1660 ($\nu$ C=C).

B. Preparation of the hydroxydioxolane (F) from 6-bromo-3,5-hexadienal dioxolane (E)

6-bromo-3-methyl-3,5-hexadienal dioxolane (E) (0.4 g, 1.7 mmol) in solution in anhydrous ether (10 ml) was introduced under argon into a 25-ml two-necked flask. The mixture was cooled to −70° C. before the addition of 1.6N tert-butyllithium (2.12 ml, 3.4 mmol) over 10 minutes. The temperature of the reaction mixture was maintained at −70° C. for 90 minutes and β-ionone (0.29 g, 1.5 mmol) was then added in solution in anhydrous ether (2 ml).

After 10 minutes at −70° C. the temperature was allowed to rise to −10° C. over 15 minutes. This temperature was maintained for 90 minutes before hydrolysing the mixture with a saturated aqueous solution (3 ml) of sodium bicarbonate. The mixture was extracted with ether (5×15 ml), and the solution was dried over magnesium sulphate and concentrated. The product was purified by flash chromatography. The following was obtained:

9-(2,6,6-Trimethyl-1-cyclohexenyl)-3,7-dimethyl-7-hydroxy-3,5,8-nonatriene dioxolane (F)

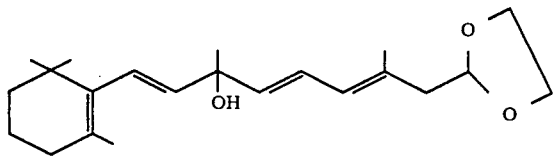

Eluent: 30/100 ether/petroleum ether.
Yld 73%. IR: 3600-3200 ($\nu$ OH); 1640 ($\nu$ C=C).

C. Hydrolysis of the hydroxydioxolane (F)

Hydroxydioxolane (0.38 g, 1.1 mmol), a solution (28 ml) of acetone (192 ml) and water (1 ml), ionol (0.02 g) and water (0.12 ml) were introduced in succession into a 50-ml three-necked round bottom flask. The mixture was heated to reflux and a solution (0.2 ml) of acetone (141 ml) and of 48% strength aqueous hydrobromic acid (3 ml) was added. The reaction was followed by thin layer chromatography. The dehydration product (Rf: 0.8) was observed first of all and, after 30 minutes' refluxing, retinal (Rf: 0.65).

After the reaction mixture had been cooled to 0° C., it was treated with a saturated aqueous solution (5 ml) of sodium bicarbonate. The mixture was extracted with pentane (5×10 ml) and the extract was dried over magnesium sulphate and concentrated. The crude product was purified by flash chromatography. Retinal was obtained.

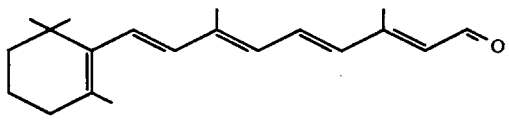

Eluent: 10/100 ether/petroleum ether.
Yld: 59%. IR: 1670 ($\nu$ C=C); 1580 ($\nu$ C=C).
Proton NMR showed the presence of two aldehyde signals in a ratio of 70/30.

EXAMPLE 3: Synthesis of a Compound of Formula (II)

A. Hydrolysis of the hydroxyacetal (C)

The crude (or purified) product of the bromination reaction of the hydroxyacetal (c) employed in dry acetone (100 ml) was introduced into a 250-ml conical flask fitted with a thermometer, a condenser and a dropping funnel. Water (1.4 ml) was then added, followed by ionol (0.2 g). The reaction mixture was heated to reflux for one minute before the introduction of a solution (1.2 ml) consisting of dry acetone (142 ml) and 48% strength aqueous hydrobromic acid (3 ml). Refluxing was continued for 40 minutes. The solution blackened from the 35th minute onwards. After disappearance of the hydroxyacetal spot in TLC, the temperature was lowered to +20° C. before the addition of pentane (100 ml). The mixture was treated with a saturated aqueous solution (10 ml) of sodium bicarbonate to bring it to a neutral pH. It was extracted with pentane (5×30 ml) and the solution was dried over magnesium sulphate and concentrated. The product was purified by flash chromatography. The following was obtained:

6-bromo-3-methyl-2,4-hexadienal (G)

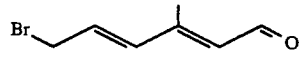

Eluent: 10/100 ether/petroleum ether.
Yld: 70%. IR: 1670 ($\nu$ C=0); 1650 ($\nu$ C=C).

B. Protection of the aldehyde functional group using an acetal group

Mixed orthoformate (17.5 mmol) prepared by mixing methyl orthoformate (21.2 g, 0.2 mol), ethylene glycol (9.3 g, 0.15 mol) and a catalytic quantity of para-toluenesulphonic acid heated to reflux and distilled was added successively to bromoaldehyde (G) (1.13 g, 5.85 mmol). A 12% strength solution (0.2 ml) of hydrogen chloride in dry methanol was introduced at room temperature. The progress of the reaction was monitored by TLC. After two hours, the reaction mixture was neutralized with sodium methylate. The solvents were evaporated off and the residue was purified by flash chromatography. The following was obtained:

6-Bromo-1,1-dimethoxy-3-methyl-2,4-hexadiene (H)

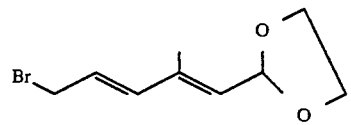

Eluent: 5/100 ether/petroleum ether.
Yld 68%. IR: 1650 ($\nu$ C=C).

EXAMPLE 4: Preparation of a compound of formula (III), 6-diethylphosphono-3-methyl-2,4-hexadienal dioxolane (I)

Triethyl phosphite (2.56 g, 15.44 mmol) in dry toluene (10 ml) and bromodioxolane (H) (3 g, 12.87 mmol) in toluene (10 ml) were introduced in succession into a 50-ml two-necked flask fitted with a thermometer and a condenser.

The reaction mixture was heated under toluene reflux for 15 hours. After complete disappearance of the bromoacetal spot in TLC and removal of the solvent, the phosphonate acetal (I) was purified by distillation under reduced pressure. The following was obtained:

6-diethylphosphono-3-methyl-2,4-hexadienal dioxolane (I)

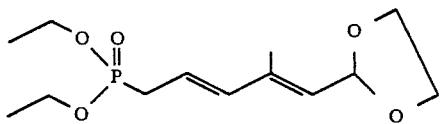

B.p.: 165° C./0.3 mm Hg.
Yld: 86%. IR: 1640-1620 ($\nu$ C=C).

A. Synthesis of Retinal

Phosphonate (I) (0.5 g, 1.72 mmol) in solution in THF (10 ml) was introduced under argon into a 25-ml two-necked flask. Potassium tert-butylate (0.275 g, 2.22 mmol) was added in small portions at −70° C. Stirring was continued at −70° C. for 90 minutes. β-ionone (0.34 g, 1.8 mmol) in solution in THF (1 ml) was then added. The solution was kept at −70° C. for 15 minutes and then at −20° C. for 1 hour.

Hydrolysis of the reaction mixture can be carried out according to two processes depending on whether it is desired to isolate retinal or its protected form.

(1) Hydrolysis for obtaining retinal

A 3N solution of hydrochloric acid (5 ml) was added at −20° C. After stirring for a quarter of an hour, the aqueous phase was extracted with ether (5×15 ml) and the extract was dried over magnesium sulphate and concentrated.

The crude product was purified by flash chromatography. Retinal was obtained.
Eluent: 10/100 ether/petroleum other.
Yld: 62%. IR: 1670 ($\nu$ C=0); 1580 ($\nu$ C=C).

Proton NMR showed the presence of two aldehyde signals in a ratio of 73/27.

(2) Hydrolysis to obtain the protected form

The reaction mixture was poured into iced water (10 ml). The following treatments were the same as above.
a. Retinal dioxolane

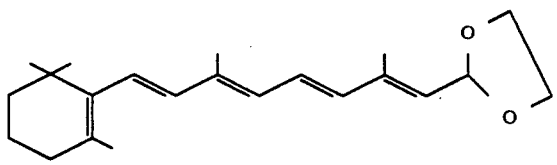

Eluent: 4/100 ether/petroleum ether.
Yld 60%. IR: 1660 ($\nu$ C=C).

Other products prepared according to the above operating procedure:
b. From acetone: Dehydrocitral dioxolane

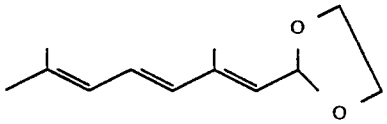

Eluent: ether/petroleum ether.
Yld 53%. IR: 1650 - 1630 - 1660 ($\nu$ C=C).
c. From methylheptenone : Dehydrofarnesal dioxolane

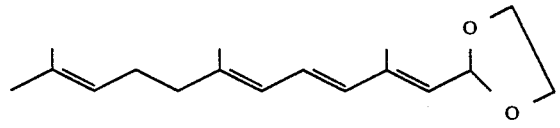

Eluent: ether/petroleum ether.
Yld: 45%. IR: 1660 - 1650 ($\nu$ C=C).
What is claimed is:
1. A compound of the formula (II):

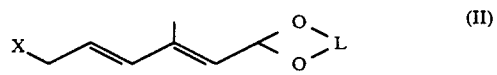

wherein L is an alkylene radical containing 2 to 3 carbon atoms, optionally substituted by one or more alkyl, alkylene or alkoxy groups containing 1 to 4 carbon atoms, and X is chlorine, bromine or iodine.

* * * * *

UNITED STATES PATENT AND TRADEMARK OFFICE
CERTIFICATE OF CORRECTION

PATENT NO. : 5,266,708
DATED : November 30, 1993
INVENTOR(S) : Pierre Chabardes et al.

It is certified that error appears in the above-indentified patent and that said Letters Patent is hereby corrected as shown below:

Inventors, Title Page, line 1, change "Charbardes" to --Chabardes--.

Claim 1, column 10, line 43, after "formula (II)" insert --used in the manufacture of Vitamin A--.

Signed and Sealed this

Sixth Day of September, 1994

Attest:

BRUCE LEHMAN

*Attesting Officer*    *Commissioner of Patents and Trademarks*